(12) United States Patent
De Man et al.

(10) Patent No.: US 7,428,292 B2
(45) Date of Patent: Sep. 23, 2008

(54) METHOD AND SYSTEM FOR CT IMAGING USING MULTI-SPOT EMISSION SOURCES

(75) Inventors: Bruno K. B. De Man, Clifton Park, NY (US); Colin R. Wilson, Niskayuna, NY (US); Bernhard Claus, Niskayuna, NY (US); Maria Iatrou, Clifton Park, NY (US); James W. LeBlanc, Niskayuna, NY (US); Dirk Bequé, Munich (DE); Samit Kumar Basu, Niskayuna, NY (US); Mark Vermilyea, Niskayuna, NY (US); Zhye Yin, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/563,061

(22) Filed: Nov. 24, 2006

(65) Prior Publication Data

US 2008/0123803 A1    May 29, 2008

(51) Int. Cl.
*G01N 23/00* (2006.01)
(52) U.S. Cl. ............................................. 378/9; 378/4
(58) Field of Classification Search .................. 378/9, 378/5, 12, 4, 37, 19
See application file for complete search history.

(56) References Cited

U.S. PATENT DOCUMENTS

| | | | |
|---|---|---|---|
| 4,196,352 A | 4/1980 | Berninger et al. | |
| 4,384,359 A | 5/1983 | Franke | |
| 4,991,190 A | 2/1991 | Mori | |
| 5,848,117 A | 12/1998 | Urchuk et al. | |
| 5,966,422 A | 10/1999 | Dafni et al. | |
| 6,421,412 B1 | 7/2002 | Hsieh et al. | |
| 6,483,892 B1 | 11/2002 | Wang et al. | |
| 6,876,719 B2 | 4/2005 | Ozaki | |
| 6,947,522 B2 | 9/2005 | Wilson et al. | |
| 6,983,035 B2 | 1/2006 | Price et al. | |
| 7,039,153 B2 | 5/2006 | Bruder et al. | |
| 7,062,006 B1 * | 6/2006 | Pelc et al. | 378/9 |
| 2003/0043957 A1 | 3/2003 | Pelc | |
| 2003/0235267 A1 * | 12/2003 | Hsieh et al. | 378/16 |
| 2004/0114710 A1 | 6/2004 | Ozaki | |
| 2004/0213371 A1 | 10/2004 | Bruder et al. | |
| 2005/0190878 A1 * | 9/2005 | De Man et al. | 378/9 |
| 2005/0226364 A1 * | 10/2005 | De Man et al. | 378/9 |
| 2005/0226371 A1 * | 10/2005 | Kautzer et al. | 378/37 |
| 2006/0002506 A1 | 1/2006 | Pelc | |
| 2006/0210015 A1 | 9/2006 | Pelc et al. | |

* cited by examiner

*Primary Examiner*—Hoon Song
(74) *Attorney, Agent, or Firm*—Eileen W. Gallagher (57) ABSTRACT

A CT imaging system includes a rotatable gantry having an opening to receive an object to be scanned. A plurality of x-ray emission sources are attached to the rotatable gantry, each x-ray emission source configured to emit x-rays in a conebeam toward the object. The CT imaging system also includes a plurality of x-ray detector arrays attached to the gantry and positioned to receive x-rays passing through the object. At least one x-ray detector array of the plurality of x-ray detector arrays is configured to receive x-rays from more than one x-ray emission source.

15 Claims, 8 Drawing Sheets

METHOD AND SYSTEM FOR CT IMAGING USING MULTI-SPOT EMISSION SOURCES

BACKGROUND OF THE INVENTION

The present invention relates generally to diagnostic imaging and, more particularly, to a method and apparatus of CT imaging using multi-spot emission sources.

Typically, in computed tomography (CT) imaging systems, an x-ray source emits a cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

It is generally desirable to have increased speed, coverage, and resolution of CT scanners. In recent years, manufacturers have improved scanners by increasing the gantry speed, by reducing the pixel size, and by extending the coverage of the detectors in the Z direction by extending the length of the detector array in the Z direction. This approach has resulted in development of CT systems that have larger detector arrays. Larger detector arrays, however, may be undesirable for a number of reasons. For instance, large detector arrays add cost and complexity to a CT system, not only in the detector components themselves, but in the data acquisition systems required to read out the increased number of channels. The increased detector array size also results in an increased mass of the overall detector, thereby resulting in increased mechanical stresses in the components of the CT system.

A complete dataset is typically acquired during a rotation of a CT gantry through approximately 180 degrees, thereby defining the temporal resolution of a CT scanner, ignoring cone angles. Accordingly, the temporal resolution may be improved by spinning the gantry faster. However, mechanical stresses therein substantially increase with increased gantry speed, thereby imposing practical limits on the upper speed of the gantry.

As detector arrays get longer in the Z direction, an increase in the cone angle occurs as well. The cone angle is the angle, along the Z direction, between the focal spot and the edges of the detector array. The increase in cone beam angle leads to cone beam artifacts in reconstructed images. Beyond a certain limit, the cone beam becomes severe, and increased scan coverage may not be accomplished by simply increasing the length of the detector array along the Z direction.

It is generally desired, as well, to obtain scan data exclusively from a cardiac region of a patient, as well from a larger patient field-of-view, while reducing the x-ray dose that a patient is exposed to during a CT scan. Traditional single spot CT scanners typically use a bowtie filter to make the detected flux somewhat uniform throughout the detector array. The bowtie filter results in scattered radiation that is not useful for the purpose of image acquisition. Because the amount of scatter radiation tends to be high for single spot CT sources, the detectors have a collimator positioned to attenuate, or block, x-rays that do not derive from the primary source. The collimator, as well, results in a loss of dose efficiency that, for given image quality, results in increased dose to the patient.

Therefore, it would be desirable to design a CT apparatus and method to improve image quality while increasing Z coverage of a subject and decreasing dose to the subject.

BRIEF DESCRIPTION OF THE INVENTION

The present invention provides a method and apparatus that overcome the aforementioned drawbacks. A plurality of x-ray emission sources and x-ray detectors are positioned such that the plurality of detectors receive x-rays from more than one x-ray emission source.

According to an aspect of the present invention, a CT imaging system includes a rotatable gantry having an opening to receive an object to be scanned. A plurality of x-ray emission sources are attached to the rotatable gantry, each x-ray emission source configured to emit x-rays in a conebeam toward the object. The CT imaging system also includes a plurality of x-ray detector arrays attached to the gantry and positioned to receive x-rays passing through the object. At least one x-ray detector array of the plurality of x-ray detector arrays is configured to receive x-rays from more than one x-ray emission source.

According to another aspect of the present invention, a method of making a CT imaging system includes attaching a plurality of x-ray sources to a rotatable CT gantry. The method further includes attaching a plurality of x-ray detector arrays to the rotatable CT gantry and configuring at least one of the x-ray detector arrays to receive x-rays from more than one x-ray source of the plurality of x-ray sources.

According to yet another aspect of the present invention, a CT imaging system includes a gantry configured to rotate about a subject. A pair of line sources is configured to emit x-rays toward the subject and a detector array configured to receive x-rays emitted from each of the pair of line sources, each passing through at least a small FOV of the subject.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a sixteen-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
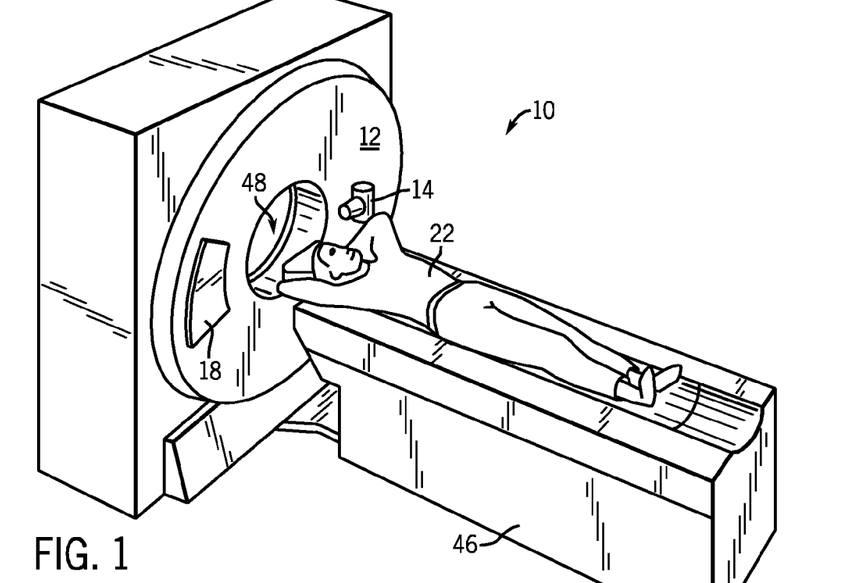
FIG. 1 is a pictorial view of a CT imaging system.
Figure 2:
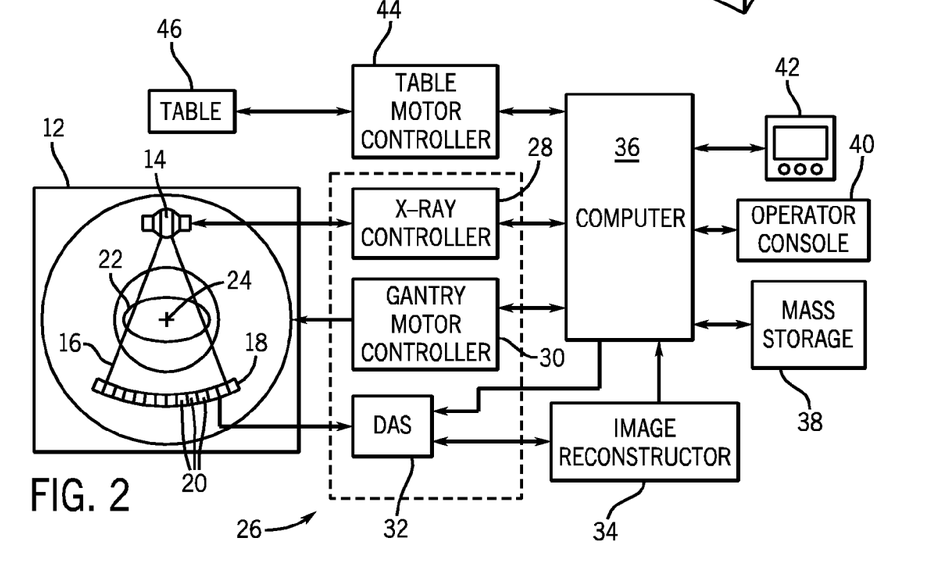
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figures 3, 4:
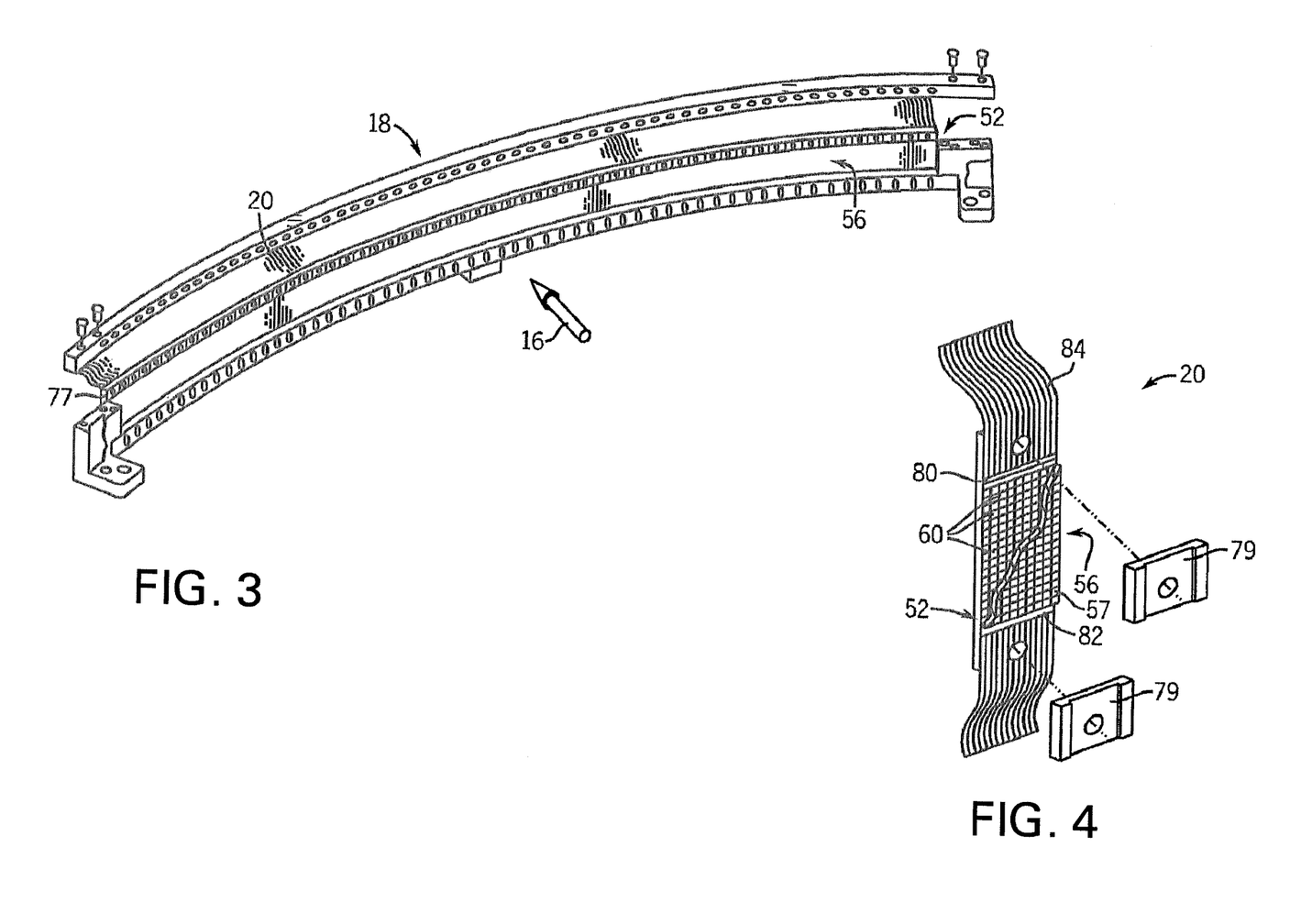
FIG. 3 is a perspective view of one embodiment of a CT system detector array.
FIG. 4 is a perspective view of one embodiment of a detector.

As shown in FIGS. 3 and 4, detector array 18 includes a plurality of scintillators 57 forming a scintillator array 56. In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

According to an embodiment of the present invention, the temporal resolution of the CT system 10 is improved by increasing the angular coverage of the system by placing multiple detectors about the gantry as described below in FIGS. 5-9. The multiple detectors are each illuminated by at least one x-ray emission source positioned in the gantry approximately opposite the detector such that x-rays emitting from the at least one x-ray emission source pass through the subject to be scanned. Accordingly, the detectors may receive data which passes through either a cardiac field-of-view of the subject, a peripheral field-of view, or a full field-of view which encompasses both.

To reduce conebeam effects, the point sources illustrated in FIGS. 5-9 may also extend in a Z-direction of the CT system, or may be line or planar sources that extend in the Z-dimension of the CT system, as well. Furthermore, planar sources can be a series of point emission sources, multiple line sources in the Z-direction, or a source that emits substantially over the face of the area of the source. In a preferred embodiment, point sources may include, but are not limited to, solid state x-ray sources, thermionic x-ray sources, field emitters, and the like. Finally, x-ray tubes may be positioned on the gantry to work in conjunction with the point, line, and area sources. An x-ray tube may be positioned as such under conditions where additional x-ray flux is desired to augment the point, line, and areas sources. The x-ray tube may be positioned along the axis of the CT system such that x-ray tube is substantially in the center of the point, line, or area sources along the Z-direction. Alternatively, the x-ray tube may be placed off-center along Z as well.

Figure 5:
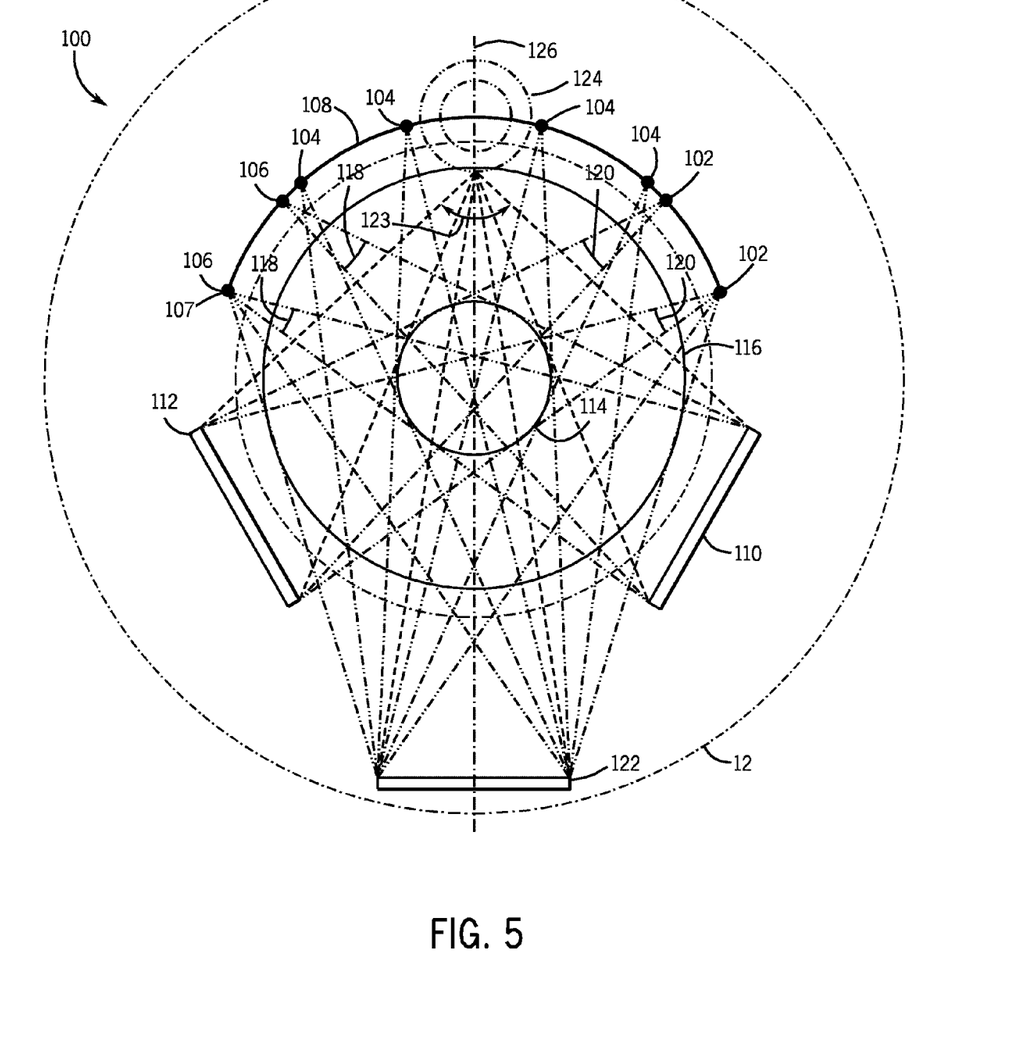
FIG. 5 is a schematic diagram of an arrangement of a plurality of emission sources and a plurality of detector arrays of a CT system according to one embodiment of the present invention.

FIG. 5 is an axial view of the gantry 12 of the CT system 10 of FIG. 1, comprising a plurality of emission sources and a plurality of detector arrays according to one embodiment. Gantry 12 includes a plurality of emission sources 102, 104, 106 positioned along arc 108. A plurality of detector arrays 110, 112, 122 is positioned to receive x-rays that emit from sources 102, 104, 106. Gantry 12 rotates about a small field-of-view (FOV), or cardiac region 114 and a large FOV 116 which encompasses both the cardiac region 114 and a peripheral region beyond cardiac region 114 out to large FOV 116. Gantry 12 is positioned such that x-ray conebeams 118 that impinge on detector array 110 from emission sources 106 pass through at least the small FOV 114 to provide full coverage thereof. Detector array 112 is positioned such that x-ray conebeams 120 that impinge on detector array 112 from emission sources 102 pass through at least small FOV 114 and provide at least full coverage thereof. Detector array 122 is positioned to receive emission from sources 102, 104, 106 which emit x-rays that pass through both the small FOV 114 and peripheral region beyond the small FOV 114 to the large FOV 116, providing full coverage thereof. In a preferred embodiment, an x-ray tube 124 is positioned along arc 108 at, for instance, a location substantially opposite detector array 122, such that high flux x-rays 123 emitting from x-ray tube 124 may impinge upon any of detector arrays 110, 112, and 122. The x-ray tube 124, the emission sources 102, 104, 106, and the plurality of detector arrays 110, 112, 122 may be substantially symmetrically aligned with respect to axis 126. Point sources 102, 104, and 106 may be directed each to a single detector array 110, 112, 122, or a single point source may be directed to multiple detector arrays, as illustrated wherein point source 107 is directed to detector arrays 110 and 122.

Figure 6:
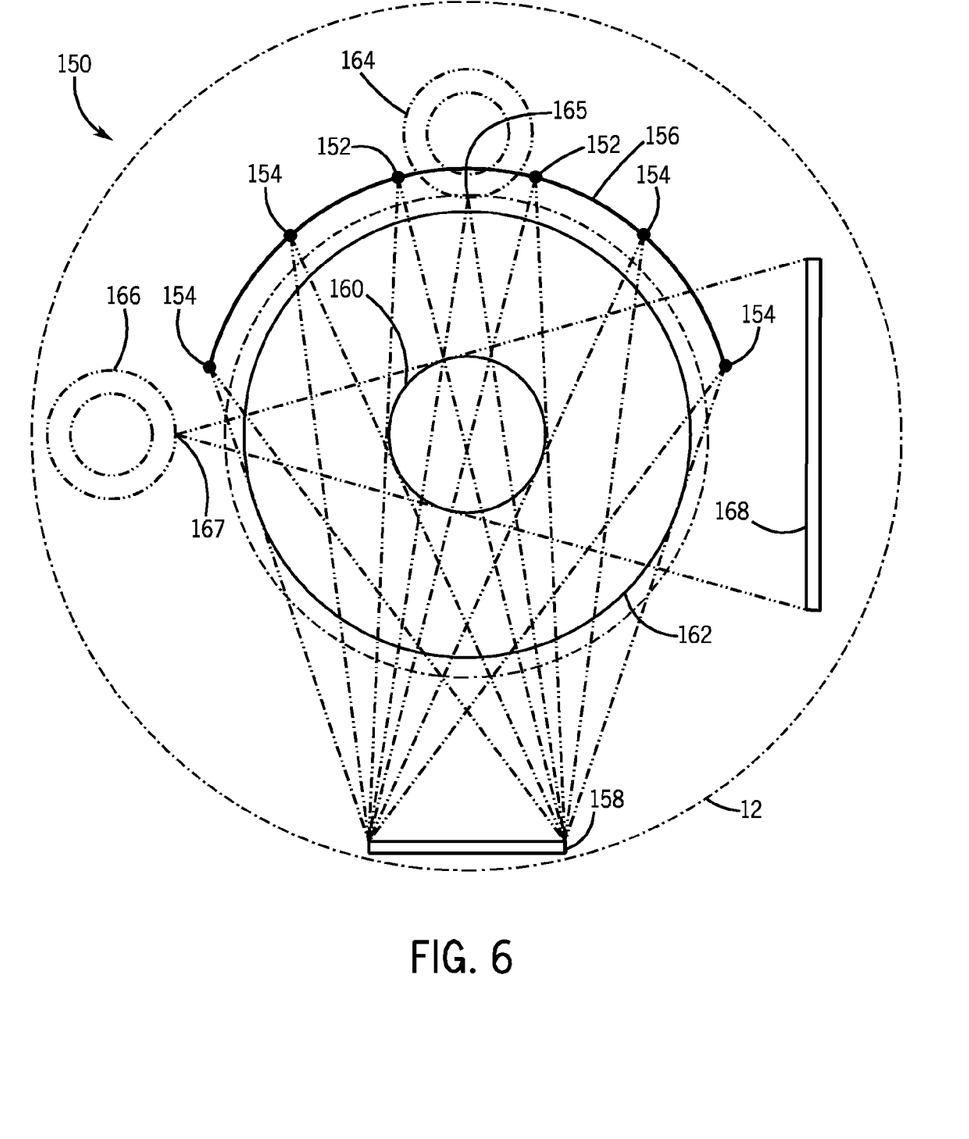
FIG. 6 is a schematic diagram of an arrangement of a plurality of emission sources and a plurality of detector arrays of a CT system according to another embodiment of the present invention.

FIG. 6 is an axial view of the gantry 12 of the CT system 10 of FIG. 1, according to another embodiment. Gantry 12 includes a plurality of emission sources 152, 154 positioned along arc 156. Detector array 158 is positioned to receive x-rays emitting from sources 152, 154. Gantry 12 rotates about a small FOV 160 and a large FOV 162. Detector array 158 is positioned to receive x-rays emitting from sources 152 that pass through at least the small FOV 160 and provide full coverage thereof. Detector array 158 is positioned to receive x-rays emitting from sources 154 that pass through at least the a peripheral region outside small FOV 160, to large FOV 162 and provide full coverage thereof. In a preferred embodiment, an x-ray tube 164 is positioned along arc 156 at, for instance, a location opposite detector array 158 such that high flux x-rays 165 emitting therefrom impinge upon detector array 158. In an alternative embodiment, an x-ray tube 166 is placed at a circumferential or radial location different from that of arc 156, and a detector array 168 is positioned opposite x-ray tube 166 such that the high flux x-rays 165 emitting from x-ray tube 166 pass through the small FOV 160 and the large FOV 162 to impinge on detector array 168. Detector 168 may be enlarged to provide large FOV coverage from x-ray tube 166. In another alternative embodiment, sources 152 may be used to pass through the small FOV 160 to detector array 158, and sources 152 may then be used in conjunction with x-ray tube 166, wherein detector 168 may be enlarged to provide coverage out to the large FOV 162 for x-rays emitting from x-ray tube 166.

Figure 7:
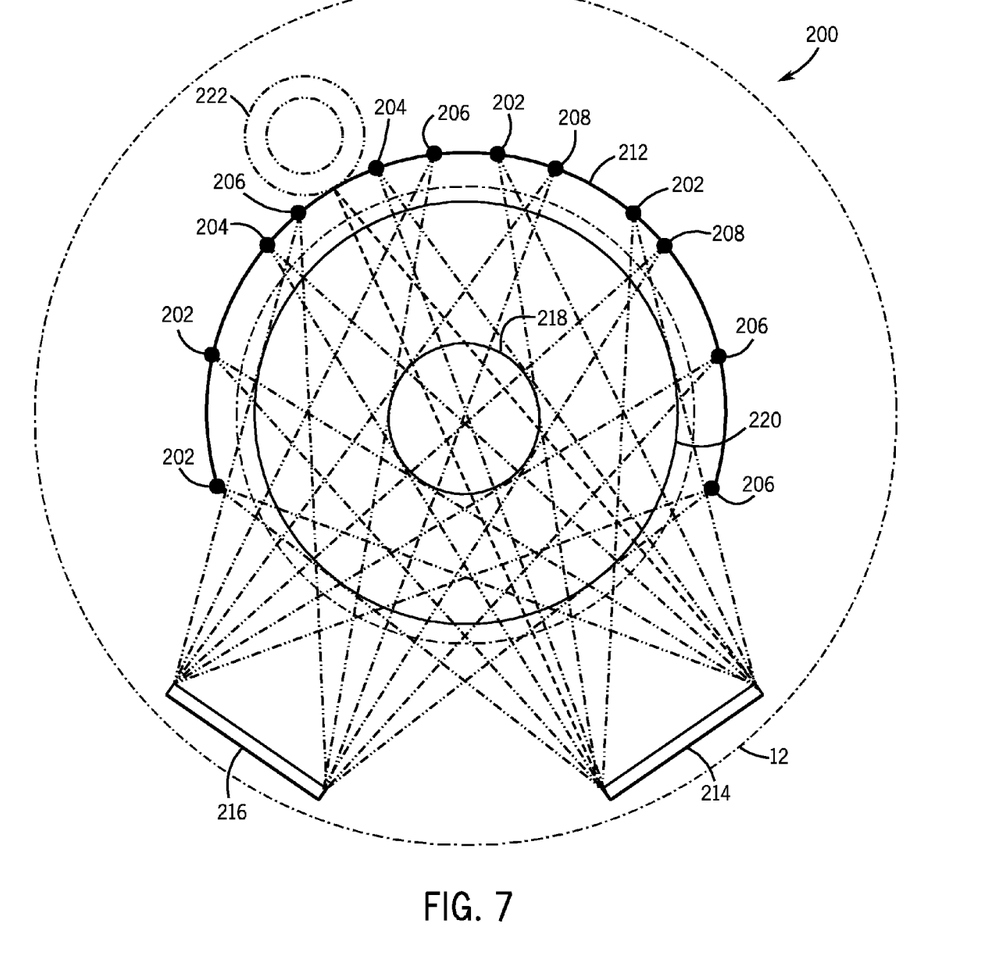
FIG. 7 is a schematic diagram of an arrangement of a plurality of emission sources and a plurality of detector arrays of a CT system according to another embodiment of the present invention.

FIG. 7 is an axial view of the gantry 12 of the CT system 10 of FIG. 1, according to another embodiment. Gantry 12 includes a plurality of emission sources 202, 204, 206, 208 positioned along arc 212. Detector array 214 is positioned opposite sources 202, 204 and is positioned to receive x-rays emitting from sources 204 which pass through at least a small FOV 218 and provide full coverage thereof. Detector array 214 is also positioned to receive x-rays from sources 202 which pass through a peripheral region outside of small FOV 218 to large FOV 220. Detector array 216 is positioned opposite sources 206, 208 and is positioned to receive x-rays emitting from sources 206 which pass through at least the small FOV 218 and provide full coverage thereof. Detector array 216 is also positioned to receive x-rays from sources 206 which pass through a peripheral region outside small FOV 218 to large FOV 220. In a preferred embodiment, an x-ray tube 222 is positioned opposite detector array 214 such that high flux x-rays 224 that emit therefrom pass through the small FOV 218 and the large FOV 220 to impinge on at least detector array 214. Detector array 214 may be enlarged to provide coverage out to the large FOV 220.

Figure 8:
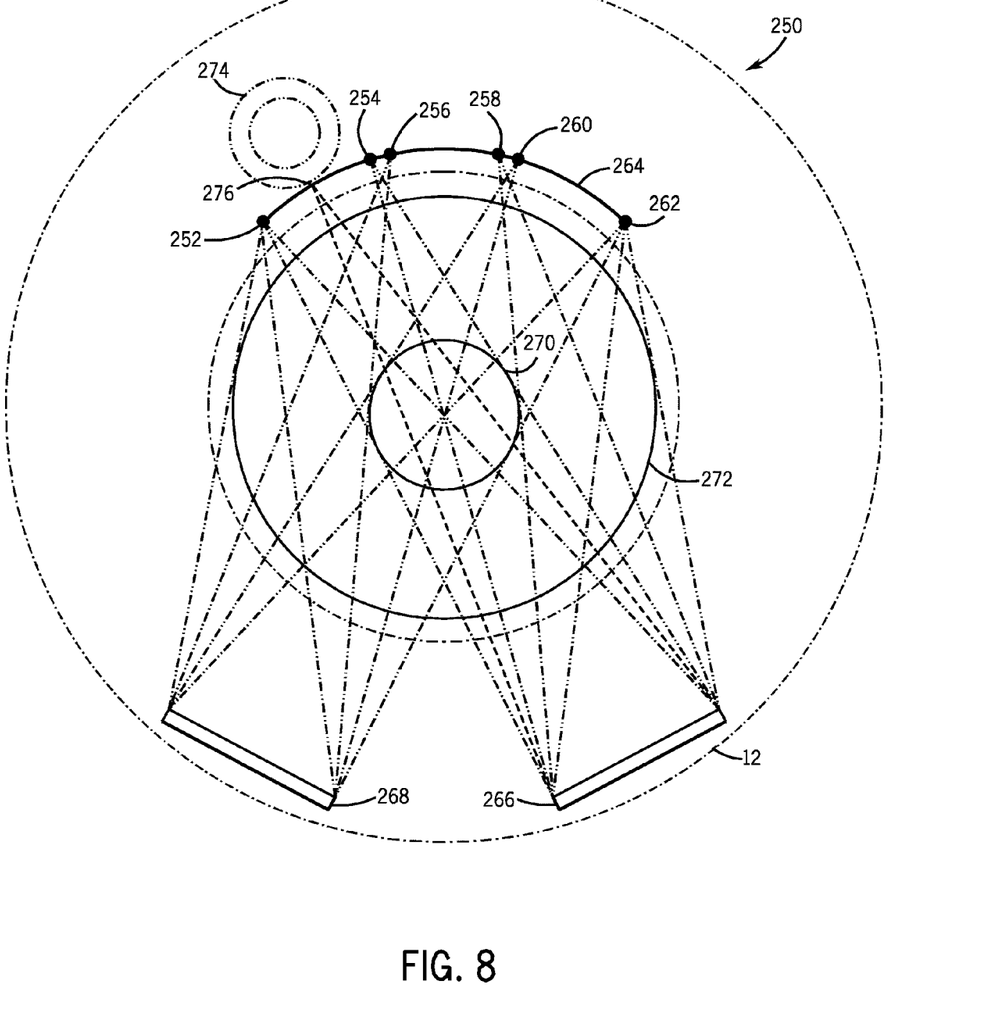
FIG. 8 is a schematic diagram of an arrangement of a plurality of emission sources and a plurality of detector arrays of a CT system according to another embodiment of the present invention.

FIG. 8 is an axial view of the gantry 12 of the CT system 10 of FIG. 1, according to another embodiment. Gantry 12 includes a plurality of emission sources 252-262 positioned along an arc 264. Detector arrays 266, 268 are positioned opposite sources 252-262 such that sources 252, 254, 258, 262 illuminate detector array 266 and sources 252, 256, 260, 262 illuminate detector array 268. Sources may be individually directed to a single detector, as between source 254 and detector array 266, or a source may be directed to two detectors, as between source 254 and detector array 268 (conebeam angle not shown). Detector array 266 is positioned such that x-rays emitting from sources 252, 254 pass through both a small FOV 270 and a large FOV 272, and that x-rays emitting from sources 258, 262 pass through at least the peripheral region outside small FOV 270 to large the FOV 272. Detector array 268 is positioned such that x-rays that emit from sources 260, 262 pass through both the small FOV 270 and the large FOV 272, and that x-rays emitting from sources 258, 262 pass through at least the peripheral region outside small FOV 270 to the large FOV 272. Preferably, an x-ray tube 274 is positioned opposite detector array 266 such that high flux x-rays 276 emitting therefrom pass through at least the small FOV 270 to impinge on detector array 266.

Figure 9:
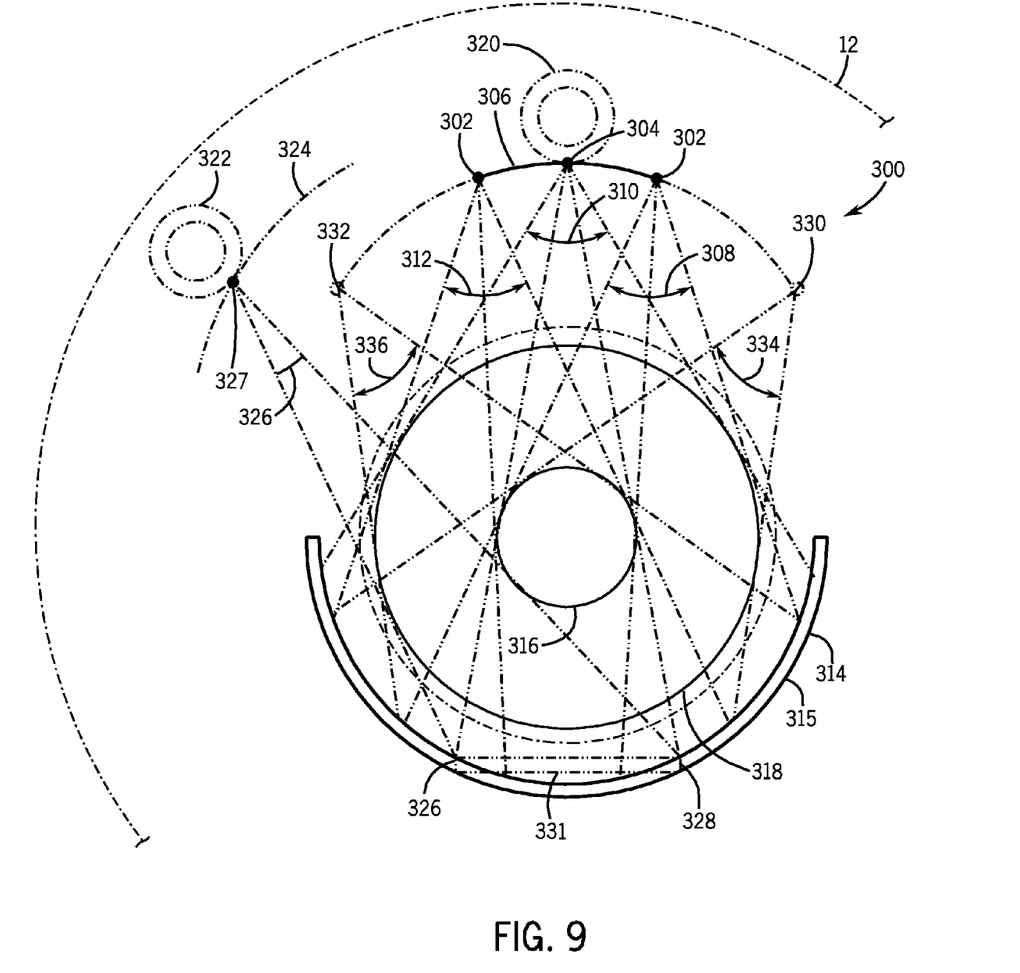
FIG. 9 is a schematic diagram of an arrangement of a plurality of emission sources and a plurality of detector arrays of a CT system according to another embodiment of the present invention.

FIG. 9 is an axial view of the gantry 12 of the CT system 10 of FIG. 1, according to another embodiment. In a preferred embodiment, gantry 12 includes a plurality of emission sources 302, 304 along an arc 306 which emit x-rays in conebeams 308, 310, 312. A detector array 314 is positioned to receive x-rays that emit from sources 302, 304 such that they pass through a small FOV 316 and a peripheral region outside the small FOV 316 to a large FOV 318. An emission source or an x-ray tube 320 is preferably positioned along arc 306 and opposite detector array 314 such that high flux x-rays 310 emitting therefrom pass through the small FOV 316 and up to the entire large FOV 318.

Referring again to FIG. 9, in an alternative embodiment, emission from emission source 320 is combined with emission from a second emission source or x-ray tube 322 wherein the second source 322 is positioned along a second arc 324 and emits a conebeam 326 to illuminate the large FOV 318. As such, x-rays from conebeam 326 impinge upon detector array 314 between points 326, 328. Accordingly, emission point 304 and/or x-rays that emit from emission source 320, in combination with x-rays 326 emitting from second emission source 322, are positioned to pass x-rays through both small FOV 316 and large FOV 318, providing full subject coverage thereof. As such, detector array 314 forming an arc as shown, between points 324 and 326, is adequate to receive signal from both locations 304 and 328. In such a configuration, flat detector array 331 may also be positioned as an alternative to a detector array 314 lying on arc 315, between 326 and 328.

Still referring to FIG. 9, in yet another alternative embodiment, emission sources 330, 332 lie on arc 306 having conebeams 334, 336 and may operate alone or in conjunction with sources 302, 304. As such, sources 330, 332 illuminate both the small FOV 316 and large FOV 318, and provide overlapping coverage of the small FOV 316, hence improving temporal resolution and image quality.

The embodiments described above in FIGS. 5-9 illustrate at least one detector array having multiple angular coverage of the scanning region, thereby increasing the temporal resolution. The embodiments also result in the ability to implement a "virtual bowtie." As such, the sources that emit from various locations that surround the patient may be grid controlled such that the mAs at each focal spot is optimized on a view-by-view basis. As such, such an operation may preempt the need for a conventional bowtie filter by selecting regions to obtain varying degrees of x-ray flux, effectively operating as a bowtie while reducing dose to the patient.

The embodiments described above also illustrate CT geometries with multiple focal spots in the Z direction, thereby reducing conebeam artifacts. With the x-ray emission sources extending in the Z direction as either a series of point sources, a line source, or a planar source as contemplated herein, Z coordinate subject coverage greater than the Z length of the detector array can be obtained. X-rays thereby impinge on the detector arrays with a reduced cone angle, thus reducing the propensity to cause conebeam-related image artifacts.

The embodiments described above also illustrate CT geometries which may operate with variable kVp operation. As an example, a first emission source, or plurality of emission sources, may be caused to operate at a first kVp, and a second emission source, or plurality of emission sources, may be caused to operate at a second kVp. Accordingly, images may be obtained wherein a first series of imaging data is acquired at the first kVp and a second series of imaging data is acquired at the second kVp. Additionally, detector arrays described herein may be operated in a simultaneous fashion to acquire x-rays passing through the object simultaneously. Alternatively, detector arrays described herein may be operated in an alternating fashion or sequentially to acquire data using x-rays which pass through the object over a short duration of time, and do not operate simultaneously.

Figure 10:
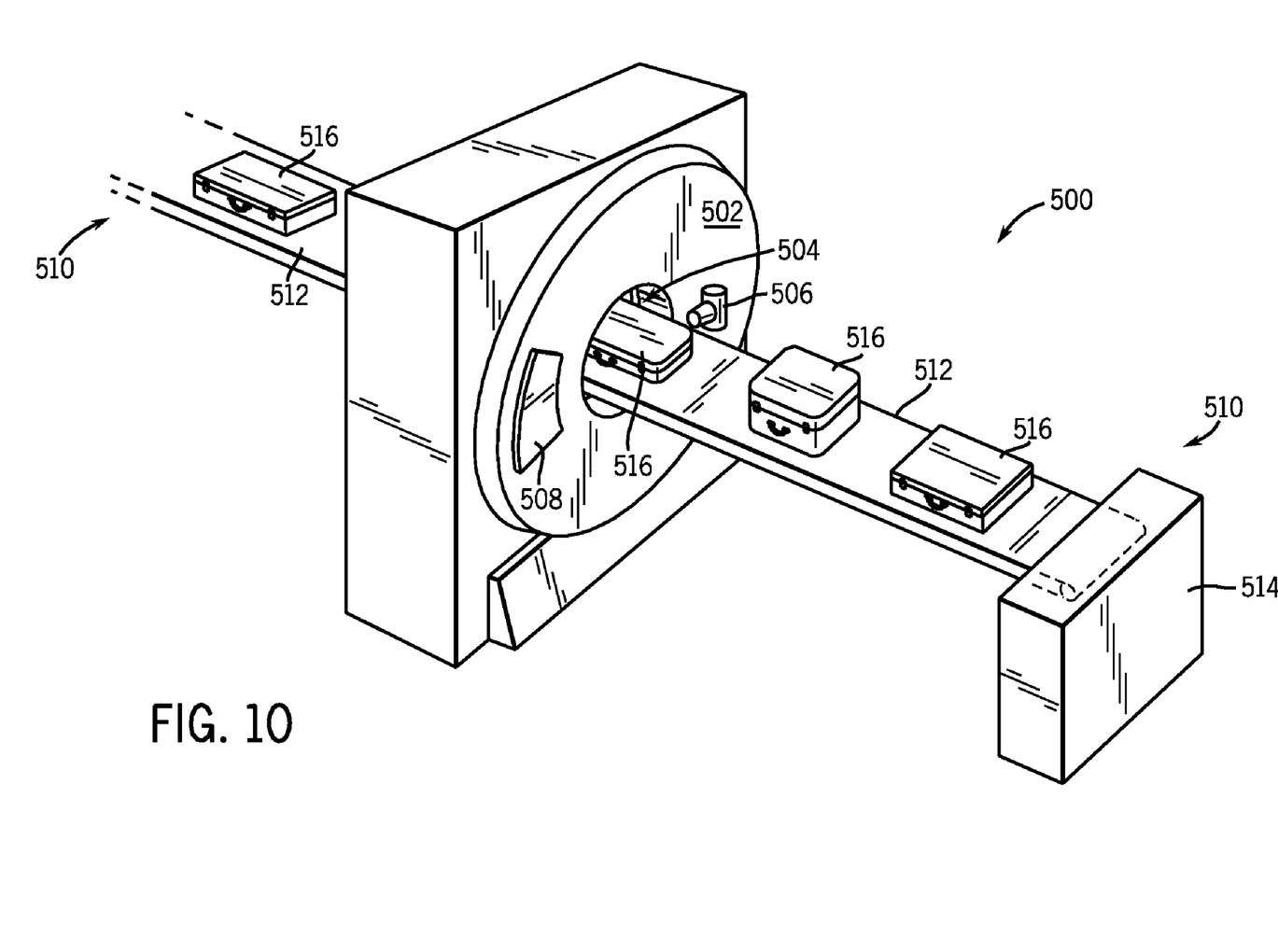
FIG. 10 is a pictorial view of a CT system for use with a non-invasive package inspection system incorporating an embodiment of the present invention.

Referring now to FIG. 10, package/baggage inspection system 500 includes a rotatable gantry 502 having an opening 504 therein through which packages or pieces of baggage may pass. The rotatable gantry 502 houses an embodiment of an emission source 506 and detector array arrangement 508 described above in any of FIGS. 5-9. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

According to one embodiment of the present invention, a CT imaging system includes a rotatable gantry having an opening to receive an object to be scanned. A plurality of x-ray emission sources are attached to the rotatable gantry, each x-ray emission source configured to emit x-rays in a conebeam toward the object. The CT imaging system also includes a plurality of x-ray detector arrays attached to the gantry and positioned to receive x-rays passing through the object. At least one x-ray detector array of the plurality of x-ray detector arrays is configured to receive x-rays from more than one x-ray emission source.

According to another embodiment of the present invention, a method of making a CT imaging system includes attaching a plurality of x-ray sources to a rotatable CT gantry. The method further includes attaching a plurality of x-ray detector arrays to the rotatable CT gantry and configuring at least one of the x-ray detector arrays to receive x-rays from more than one x-ray source of the plurality of x-ray sources.

According to yet another embodiment of the present invention, a CT imaging system includes a gantry configured to rotate about a subject. A pair of line sources is configured to emit x-rays toward the subject and a detector array configured to receive x-rays emitted from each of the pair of line sources, each passing through at least a small FOV of the subject.

The present invention has been described in terms of the preferred embodiment, and it is recognized that equivalents, alternatives, and modifications, aside from those expressly stated, are possible and within the scope of the appending claims.

What is claimed is:

1. A CT imaging system comprising:
   a rotatable gantry having an opening to receive an object to be scanned;
   a plurality of x-ray emission sources attached to the rotatable gantry, each x-ray emission source configured to emit x-rays in a conebeam toward the object, wherein a portion of the x-rays pass through a region of interest within the object; and
   at least two x-ray detector arrays positioned at more than one position about the gantry wherein each detector array is positioned at an angular offset with respect to each other detector array such that each x-ray detector array receives x-rays that are emitted from at least two separate x-ray emission sources and pass through the region of interest to improve temporal resolution of the region of interest.

2. The CT imaging system of claim 1 wherein at least one of the plurality of x-ray emission sources is an x-ray tube.

3. The CT imaging system of claim 1 wherein the plurality of x-ray emission sources are symmetrically positioned with respect to the plurality of x-ray detector arrays.

4. The CT imaging system of claim 1 wherein the plurality of x-ray emission sources are accurately positioned equidistant from a center point.

5. The CT imaging system of claim 4 wherein the center point is a center of rotation of the gantry.

6. The CT imaging system of claim 1 wherein at least one of the plurality of x-ray emissions sources is a line source.

7. The CT imaging system of claim 1 wherein at least one of the plurality of x-ray emission sources comprises one of a solid state x-ray source, a thermionic x-ray source, and a field emitter.

8. The CT imaging system of claim 1 wherein the region of interest comprises a cardiac region of the object.

9. A method of making a CT imaging system, the method comprising the steps of:
- attaching a plurality of x-ray sources to a rotatable CT gantry to emit a plurality of conebeam x-rays, wherein a portion of the x-rays pass through a region of interest within the object; and
- attaching at least two x-ray detector arrays at more than one position about the rotatable CT gantry, wherein each detector array is positioned at an angular offset with respect to each other detector array such that each x-ray detector array receives x-rays-that are emitted from at least two separate emission sources and pass through the region of interest;

to improve temporal resolution of the region of interest.

10. The method of claim 9 further comprising the step of configuring the x-ray detector arrays to fully acquire data of a cardiac region of interest from no more than two x-ray sources.

11. The method of claim 9 further comprising the step of configuring the x-ray detector arrays to fully acquire data of a cardiac region of interest from only one of the x-ray sources.

12. The method of claim 9 wherein the step of attaching the plurality of x-ray sources comprises attaching an x-ray tube having a rotating anode to the rotatable CT gantry.

13. The method of claim 9 further comprising the step of symmetrically aligning the plurality of x-ray sources about an axis of symmetry.

14. The method of claim 9 further comprising the step of symmetrically aligning the x-ray detector arrays about an axis of symmetry.

15. The method of claim 9 wherein the step of attaching the plurality of x-ray sources comprises attaching at least one line source to the rotatable CT gantry.

* * * * *